United States Patent [19]

Baba et al.

[11] Patent Number: 5,296,634
[45] Date of Patent: Mar. 22, 1994

[54] METHOD FOR PREPARING 4-ALKYLSULFONYL-2-CHLORO-M-XYLENE

[75] Inventors: Masatoshi Baba; Eiichi Oya, both of Funabashi, Japan

[73] Assignee: Nissan Chemical Industries Ltd., Tokyo, Japan

[21] Appl. No.: 932,221

[22] Filed: Aug. 19, 1992

Related U.S. Application Data

[62] Division of Ser. No. 773,431, Oct. 9, 1991, Pat. No. 5,189,224.

[30] Foreign Application Priority Data

Oct. 19, 1990 [JP] Japan .................................. 2-282961

[51] Int. Cl.$^5$ .............................................. C07C 315/04
[52] U.S. Cl. ............................................ 568/28; 568/35
[58] Field of Search ............................ 562/28; 568/35

[56] References Cited

U.S. PATENT DOCUMENTS

| | | | |
|---|---|---|---|
| 2,010,754 | 7/1933 | Felix et al. | 568/28 |
| 3,879,472 | 4/1975 | Martin | 568/28 |
| 4,675,447 | 6/1987 | Ludvik | 568/28 |

FOREIGN PATENT DOCUMENTS

| | | | |
|---|---|---|---|
| 042359 | 3/1984 | Japan | 568/28 |
| 2169564 | 6/1990 | Japan | |

OTHER PUBLICATIONS

March, Advanced Organic Chemistry, pp. 510–511, 1983.

Chemical Abstracts, vol. 113, No. 21, p. 678, Nov. 19, 1990, & JP-A-2-169 564, Tsukasa Ishikura, "2–Chloro–4–Methylsulfonyl-m-Xylene and its Preparation", 113: 190914y.

*Primary Examiner*—Marianne M. Cintins
*Assistant Examiner*—Margaret J. Page
*Attorney, Agent, or Firm*—Oblon, Spivak, McClelland, Maier & Neustadt

[57] ABSTRACT

The present invention provides a method for preparing a 4-alkylsulfonyl-2-chloro-m-xylene useful as an intermediate for agricultural chemicals.

8 Claims, No Drawings

METHOD FOR PREPARING 4-ALKYLSULFONYL-2-CHLORO-M-XYLENE

This is a continuation, of application Ser. No. 07/773,431, filed on Oct. 9, 1991 now: U.S. Pat. No. 5,189,224.

The present invention relates to a novel method for preparing a 4-alkylsulfonyl-2-chloro-m-xylene useful as an intermediate for agricultural chemicals and an intermediate for the production.

It is known from Japanese Unexamined Patent Publication Nos. 61349/1988, 308069/1988 and 169564/1990 that a 4-alkylsulfonyl-2-chloro-m-xylene is an important intermediate for agricultural chemicals.

Heretofore, the following method is known as a method for preparing a 2-chloro-4-methylsulfonyl-m-xylene (Japanese Unexamined Patent Publication No. 169564/1990).

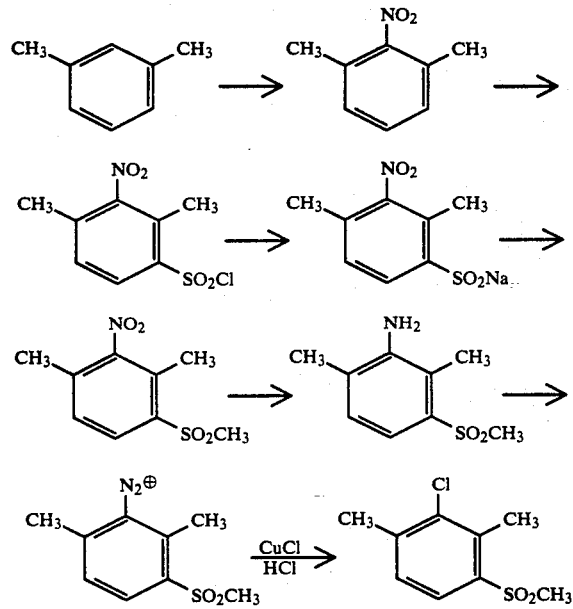

However, this method has a disadvantage that the yield of the first nitration is very low (about 15%) and also has a problem that a copper ion polluting environment is used in the last substitution of an amino group to a chlorine atom.

In order to solve the above problem, the present inventors have studied and found a novel method for preparing a 4-alkylsulfonyl-2-chloro-m-xylene (E) by way of novel precursors such as a 4-alkylsulfonyl-6-bromo-m-xylene (D-1) and a 4-alkylsulfonyl-6-bromo-2-chloro-m-xylene (D-2) by using a 4-bromo-m-xylene (A) easily obtainable by bromination of m-xylene as a starting material, as shown in the following reaction formula:

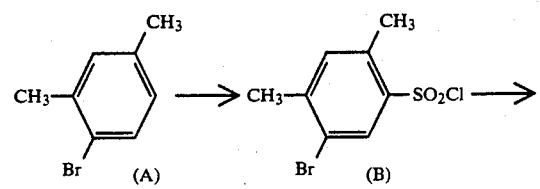

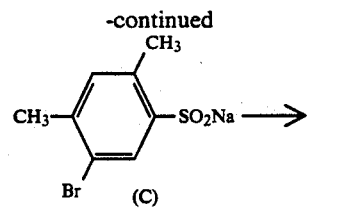

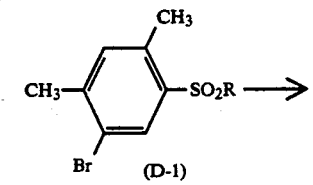

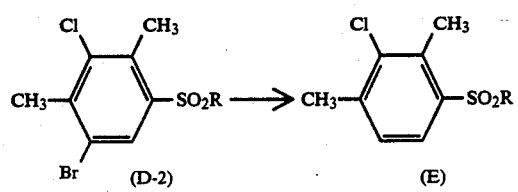

(wherein R is a $C_{1-4}$ alkyl group or a $C_{3-8}$ cycloalkyl group).

Examples of R in the present invention include a methyl group, an ethyl group, an n-propyl group, an i-propyl group, an n-butyl group, an i-butyl group, an s-butyl group, a t-butyl group, an n-pentyl group, an i-pentyl group, an s-pentyl group, a t-pentyl group, a neopentyl group, an n-hexyl group, an i-hexyl group, an s-hexyl group, an n-heptyl group, an n-octyl group, a cyclopropyl group, a cyclobutyl group, a cyclopentyl group, a cyclohexyl group, a cycloheptyl group, a cyclooctyl group and a 2,6-dimethylcyclohexyl group.

However, the present invention is not limited these products.

The method of the present invention is hereinafter explained in more detail.

The reaction of from (A) to (B) can be easily conducted by using from 2 to 10 equivalents, preferably from 2 to 5 equivalents of chlorosulfonic acid in the absence of a solvent or in the presence of a solvent inert to the reaction. Examples of the solvent include water, sulfuric acid, halogenated hydrocarbons such as methylene chloride, chloroform, carbon tetrachloride and 1,2-dichloroethane, aromatic hydrocarbons such as nitrobenzene, dimethylformamide and dimethylsulfoxide, and the reaction is preferably carried out in the absence of a solvent or in the presence of the above-mentioned halogenated hydrocarbons. The reaction temperature is generally from −30 to 200° C., preferably from 0 to 100° C. The reaction time is generally from 5 minutes to 1,000 hours, preferably from ten minutes to 15 hours.

The reaction of from (B) to (C) is carried out at a high yield by using from 1 to 10 equivalents, preferably from 1 to 5 equivalents of a reducing agent in a solvent inert to the reaction. Examples of the reducing agent include sodium sulfite and sodium hydrogen sulfite. Examples of the solvent include water, dimethylformamide, dimethylsulfoxide and the like, and a preferable solvent is water. The reaction temperature is generally from −30 to 200° C., preferably from 0 to 100° C. The reaction time is generally from 5 minutes to 200 hours, preferably from 10 minutes to 10 hours.

The reaction of from (C) to (D-1) can be easily conducted by using from 1 to 10 equivalents, preferably from 1 to 3 equivalents of an alkylating agent in the absence of a solvent or in the presence of a solvent inert to the reaction. Examples of the alkylating agent include halogenated alkyls such as methyl chloride, methyl bromide, methyl iodide, ethyl chloride, ethyl bromide and ethyl iodide, and alkyl sulfates such as dimethyl sulfate and diethyl sulfate. Examples of a solvent include water, alcohols such as methanol, ethanol, n-propanol, isopropanol, n-amylalcohol and ethylene glycol, halogenated hydrocarbons such as methylene chloride, chloroform, carbon tetrachloride and 1,2-dichloroethane, aromatic hydrocarbons such as benzene, toluene and xylene, ethers such as ethyl ether, diisopropyl ether, tetrahydrofuran and 1,4-dioxane, esters such as methyl acetate, ethyl acetate and methyl propionate, ketones such as acetone, high molecular solvent such as polyethylene glycol, acetonitrile, dimethylformamide, and dimethylsulfoxide, and they may be used in a mixture of two or more members. Among them, preferable examples include water, the above-mentioned alcohols, halogenated hydrocarbons and aromatic hydrocarbons. The present reaction provides the aimed product at a satisfactory yield generally in the absence of the catalyst, but the reaction time can be reduced and the yield can be improved by adding metallic copper or a quaternary ammonium halide such as tetrabutylammonium chloride, tetrabutylammonium bromide and trimethylbenzylammonium bromide in an amount of from 0.1 to 10% to 1 mol of the substrate. The reaction temperature is generally from $-30$ to $200°$ C., preferably from 0 to $100°$ C. The reaction time is generally from 10 minutes to 200 hours, preferably from 10 minutes to 100 hours.

Also, (D-1) can be obtained by reacting (C) with from 1 to 10 equivalents, preferably from 1 to 3 equivalents of $\alpha$-halogeno aliphatic acid or $\alpha$-halogeno aliphatic acid ester, and when reacted with the acid, decarboxylation is carried out, and when reacted with the acid ester, hydrolysis is firstly carried out and decarboxylation is then carried out. Examples of the $\alpha$-halogeno aliphatic acid or the $\alpha$-halogeno aliphatic acid ester include chloroacetic acid, methyl chloroacetate, ethyl chloroacetate, propyl chloroacetate, butyl chloroacetate, isobutyl chloroacetate, bromoacetic acid, methyl bromoacetate, ethyl bromoacetate, propyl bromoacetate, butyl bromoacetate, isobutyl bromoacetate and their alkali metal salts. Examples of the solvent include water, alcohols such as methanol, ethanol, n-propanol, isopropanol, n-amylalcohol and ethylene glycol, halogenated hydrocarbons such as methylene chloride, chloroform, carbon tetrachloride and 1,2-dichloroethane, aromatic hydrocarbons such as benzene, toluene and xylene, ethers such as ethyl ether, diisopropyl ether, tetrahydrofuran and 1,4-dioxane, esters such as methyl acetate, ethyl acetate and methyl propionate, ketones such as acetone, a high molecular solvent such as polyethylene glycol, acetonitrile, dimethylformamide and methylsulfoxide, and among them, preferable examples include water, the above-mentioned alcohols, halogenated hydrocarbons and aromatic hydrocarbons. The reaction temperature is generally from $-30$ to $200°$ C., preferably from 0 to $150°$ C. The reaction time is generally from 30 minutes to 200 hours, preferably from 30 minutes to 100 hours. Taking an example, for instance, 4-bromo-6-methylsulfonyl-m-xylene is formed by reacting the compound (C) with chloroacetic acid as an $\alpha$-halogeno aliphatic acid.

The reaction of from (D-1) to (D-2) is carried out by using from 1 to 10 equivalents, preferably from 1 to 3 equivalents of a chlorinating agent in the absence of a solvent or in the presence of a solvent inert to the reaction. Examples of the chlorinating agent include chlorine, hypochlorous acid, sulfuryl chloride, N-chlorosuccinimide, trichloroisocyanuric acid and the like. The reaction time can be reduced and the yield can be improved by using an appropriate catalyst. Preferable examples of the catalyst include a Lewis acid such as iron trichloride and aluminium chloride, metal such as iron powder, iodine, disulfur dichloride and the like. The reaction can be accelerated and the yield can be improved by adding an appropriate base. Examples of the base include inorganic bases such as sodium hydroxide, potassium hydroxide, sodium carbonate and potassium carbonate, and organic bases such as triethylamine and pyridine. Examples of the solvent include halogenated hydrocarbons such as methylene chloride, chloroform, carbon tetrachloride, and 1,2-dichloroethane, aromatic hydrocarbons such as nitrobenzene, inorganic acids such as hydrochloric acid, sulfuric acid and fuming sulfuric acid, organic acids such as acetic acid, and carbon disulfide, and among them, preferable examples include nitrobenzene, sulfuric acid, fuming sulfuric acid and the above-mentioned halogenated hydrocarbons. The reaction temperature is generally from $-50$ to $200°$ C., preferably from $-30$ to $150°$ C. The reaction time is generally from 5 minutes to 100 hours, preferably from 15 minutes to 30 hours.

The reaction of from (D-2) to (E) is carried out by using a reducing agent. Examples of the reducing method include catalytic hydrogenation and reduction by a reagent.

The catalytic hydrogenation is carried out in the presence of a catalyst in a solvent inert to the reaction. Examples of the catalyst include those disclosed in "Shin-jikken Kagaku Koza", Vol. 15-II, published by Maruzen (1976), and preferable examples include palladium, platinum, ruthenium, rhodium, Raney nickel, platinum oxide, ruthenium oxide or the like supported on a suitable carrier such as active carbon. The addition of a suitable base to remove hydrogen bromide formed, often provides a satisfactory result. Examples of the base include sodium hydroxide, potassium hydroxide, inorganic salts such as sodium carbonate, potassium carbonate, sodium hydrogen carbonate and potassium hydrogen carbonate, metal salts of carboxylic acid such as sodium acetate and potassium acetate, and organic bases such as triethylamine and pyridines. Examples of the solvent include alcohols such as methanol and ethanol, ethers such as isopropyl ether, tetrahydrofuran and 1,4-dioxane, organic acids such as acetic acid, water, N,N-dimethylformamide, and cyclohexane. The reaction temperature may be varied depending on a catalyst, a solvent, a base and the like used, but is generally from $-50$ to $200°$ C., preferably from 0 to $100°$ C. The hydrogen pressure may be varied depending on a catalyst, a solvent, a base and the like used, but is generally from normal pressure to 100 atms, preferably from normal pressure to 30 atms. The reaction time may be varied depending on the reaction conditions, but is generally from 10 minutes to 300 hours, preferably from 10 minutes to 100 hours.

Examples of the reduction by a reagent include reduction (debromination) by nascent hydrogen generated by adding metal sodium to ammonia or alcohol or mixture thereof, reduction by hydrazine, reduction by electrolysis, reduction by triethylsilane, and reduction by sodium boron hydride and lithium aluminium hydride.

The present invention is further explained hereinafter by Examples. However, the present invention is not limited thereto.

EXAMPLE 1

Synthesis of 4-bromo-6-methylsulfonyl-m-xylene 6 g of common salt was added to 25 ml of 1,2-dichloroethane (EDC), and 40 g of chlorosulfonic acid was added dropwise thereto at room temperature under stirring and 20 ml of EDC was further added thereto. To the resultant mixture, was dropwise added 18.5 g (0.1 mol) of 4-bromo-m-xylene at room temperature over one hour period. After dropwise added, the resultant mixture was stirred continuously for 30 minutes, and was then heated to 70° C., and was stirred continuously for one hour, and thereafter stood to cool to room temperature. After dropping the resultant reaction liquor to 65 ml of water, the mixture was stirred for 30 minutes and EDC layer was taken out. To a solution having 17 g of sodium carbonate and 13 g of sodium sulfite dissolved in 85 ml of water, was dropwise added the EDC layer thus obtained at 65° C. over one hour period, and the resultant mixture was stirred at the same temperature for 4 hours to take the aqueous layer out. 14.2 g of methyl iodide was added dropwise to the aqueous layer thus obtained, and the resultant mixture was heated to 65° C. to react for 4 hours.

After allowing to stand to cool to room temperature, the crystal precipitated was filtered out, and the filtered crystal was subjected to washing with water and drying to obtain 21.3 g of a crude product (purity measured by gas chromatography: 99.1%). A part of the crude product was recrystallized from methanol to obtain the above-identified aimed compound.

Melting point: 109–111° C.

$^1$HNMR (CDCl$_3$) σ (ppm): 2.42(3H,S), 2.60(3H,S), 3.06(3H,S), 7.21(1H,S), 8.14(1H,S)

EXAMPLE 2

Synthesis of 4-bromo-6-methylsulfonyl-m-xylene

In the procedure of Example 1, in place of dropping 14.2 g of methyl iodide to react at 65° C. for 4 hours, 11.7 g of sodium chloroacetate was added, and heated under reflux for 12 hours to obtain 19.4 g of a crude product of the aimed compound (purity measured by gas chromatography: 98.9%).

EXAMPLE 3

Synthesis of 2-chloro-4-bromo-6-methylsulfonyl-m-xylene 2.0 g of the crude 4-bromo-6-methylsulfonyl-m-xylene obtained in Example 1 was added to 8 ml of 20% fuming sulfuric acid. A chlorine gas was flown little by little while stirring at room temperature in a reactor provided with a dry ice trap at the upper part. After one hour, the reaction liquor was added to ice, and was extracted twice with 30 ml of EDC. The EDC solution was washed with 50 ml of water and then with 20 ml of a saturated aqueous solution of common salt, and was dried over anhydrous sodium sulfate, concentrated under reduced pressure and dried to a solid, thus obtaining 2.2 g of a crude product of the above-identified aimed compound (purity measured by gas chromatography: 81.6%). A part of the crude product was recrystallized from methanol to obtain the above-identified aimed compound.

Melting point: 124–126° C.

$^1$HNMR (CDCl$_3$) σ (ppm): 2.58(3H,S), 2.69(3H,S), 3.05(3H,S), 8.06(1H,S)

EXAMPLE 4

Synthesis of 2-chloro-4-methylsulfonyl-m-xylene 30 ml of ethanol was added to 1.0 g of the crude 2-chloro-4-bromo-6-methylsulfonyl-m-xylene obtained in Example 3, and 0.1 g of 5% palladium active carbon and 1.0 g of anhydrous sodium acetate were further added thereto. The reactor was sealed, and was substituted with hydrogen, then stirring at room temperature for 7 hours. 30 ml of water was added to the reaction liquor, and was concentrated under reduced pressure. 30 ml of EDC was further added thereto, and the resultant mixture was filtered. The EDC layer was taken out from the filtrate, and was washed with 20 ml of water and then with 10 ml of a saturated aqueous solution of common salt, and was dried over anhydrous sodium sulfate. The EDC layer thus obtained was concentrated under reduced pressure and was dried to a solid to obtain 0.7 g of a crude product of the above-identified aimed compound (purity measured by gas chromatography: 75.6%). The crude product thus obtained was recrystallized by methanol to obtain the above-identified aimed compound.

Melting point: 116–119° C.

$^1$HNMR (CDCl$_3$) σ (ppm): 2.42(3H,S), 2.72(3H,S), 3.04(3H,S), 7.17(1H,d), 7.76(2H,d)

We claim:

1. A method for preparing a 4-alkylsulfonyl-2-chloro-m-xylene of the formula (E):

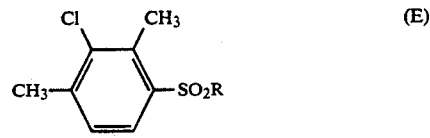

wherein R is a $C_{1-8}$ alkyl group or a $C_{3-8}$ cycloalkyl group, which comprises reacting a reducing agent with a 4-alkylsulfonyl-6-bromo-2-chloro-m-xylene of the formula (D-2):

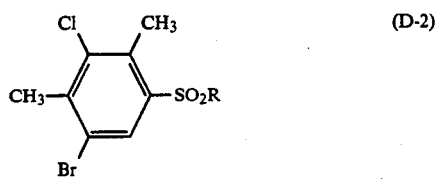

wherein R is as defined above and the reducing agent comprises hydrogen and one or more catalysts selected from the group consisting of palladium, platinum, ruthenium, Raney nickel, platinum oxide and ruthenium oxide.

2. The method for preparing the 4-alkylsulfonyl-2-chloro-m-xylene according to claim 1, wherein R is a $C_{1-4}$ alkyl group.

3. A method for preparing a 4-alkylsulfonyl-6-bromo-2-chloro-m-xylene of the formula (D-2):

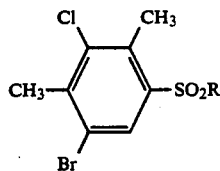

wherein R is a $C_{1-8}$ alkyl group or a $C_{3-8}$ cycloalkyl group, which comprises reacting a chlorinating agent with a 4-alkylsulfonyl-6-bromo-m-xylene of the formula (D-1):

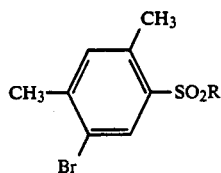

wherein R is as defined above and the chlorinating agent is one or more members selected from the group consisting of chlorine, hypochlorous acid, sulfuryl chloride, N-chlorosuccinimide and trichloroisocyanuric acid.

4. The method for preparing the 4-alkylsulfonyl-6-bromo-2chloro-m-xylene according to claim 3, wherein R is a $C_{1-4}$ alkyl group.

5. The method according to claim 3, wherein the 4-alkylsulfonyl-6-bromo-m-xylene of the formula (D-1):

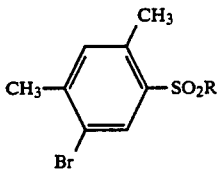

wherein R is a $C_{1-8}$ alkyl group or a $C_{3-8}$ cycloalkyl group, is prepared by reacting an alkylating agent with sodium 5-bromo-2,4-dimethylbenzenesulfinate of the formula (C):

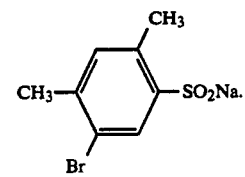

6. The method for preparing the 4-alkylsulonyl-6-bromo-m-xylene according to claim 5, wherein R is a $C_{1-4}$ alkyl group.

7. The method for preparing the 4-alkylsulfonyl-6-bromo-m-xylene according to claim 5, wherein the alkylating agent is halogenated $C_{1-4}$ alkyl, di($C_{1-4}$ alkyl)sulfate, α-halogen $C_{2-5}$ aliphatic acid, and $C_{1-4}$ alkyl ester of α-halogens $C_{2-5}$ aliphatic or an alkali metal salt of α-halogens $C_{2-5}$ aliphatic acid, and when the sodium 5-bromo-2,4-dimethylbenzenesulfinate of the formula (C) is reacted with an acid, decarboxylation is carried out, and when the sodium 5-bromo-2,4-dimethylbenzenesulfinate of the formula (C) is reacted with an acid ester, hydrolysis is carried out prior to decarboxylation.

8. The method for preparing the 4-alkylsulfonyl-6-bromo-m-xylene according to claim 7, wherein the alkylating agent is methyl chloride, methyl bromide, methyl iodide, ethyl chloride, ethyl bromide, ethyl iodide, dimethyl sulfate, diethyl sulfate, chloroacetic acid, methyl chloroacetate, ethyl chloroacetate, propyl chloroacetate, butyl chloroacetate, isobutyl chloroacetate, bromoacetic acid, methyl bromoacetate, ethyl bromoacetate, propyl bromoacetate, butyl bromoacetate, isobutyl bromoacetate, an alkali metal salt of chloroacetic acid or an alkali metal salt of bromoacetic acid.

* * * * *

UNITED STATES PATENT AND TRADEMARK OFFICE
CERTIFICATE OF CORRECTION

PATENT NO. : 5,296,634
DATED : March 22, 1994
INVENTOR(S) : Masatoshi Baba et al It is certified that error appears in the above-indentified patent and that said Letters Patent is hereby corrected as shown below:

On title page, Abstract should read as follows: "The present invention provides a method for preparing a 4-alkylsulfonyl-2-chloro-m-xylene useful as an intermediate for agricultural chemicals." should read --The present invention provides a method for preparing a 4-alkylsulfonyl-2-chloro-m-xylene useful as an intermediate for agricultural chemicals, and an intermediate for the production. The method of the present invention is to produce (E) from (C) by way of novel intermediates (D-1) and (D-2).

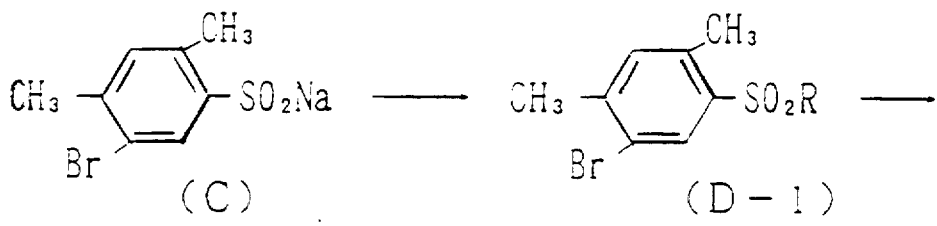

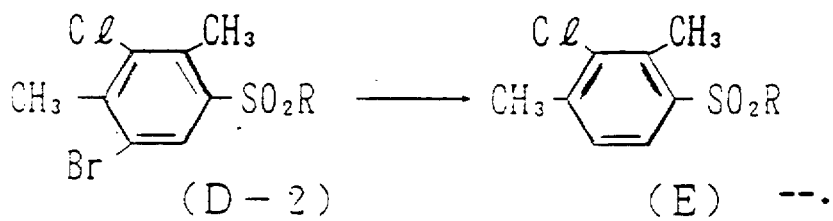

UNITED STATES PATENT AND TRADEMARK OFFICE
CERTIFICATE OF CORRECTION

PATENT NO. : 5,296,634
DATED : March 22, 1994
INVENTOR(S) : Masatoshi Baba et al It is certified that error appears in the above-indentified patent and that said Letters Patent is hereby corrected as shown below:

Column 2, line 37, "not limited these" should read --not limited to these--.

Signed and Sealed this

Twenty-ninth Day of November, 1994

Attest:

BRUCE LEHMAN

Attesting Officer

Commissioner of Patents and Trademarks